US006825164B1

(12) United States Patent
Stern et al.

(10) Patent No.: US 6,825,164 B1
(45) Date of Patent: Nov. 30, 2004

(54) METHOD TO INCREASE CEREBRAL BLOOD FLOW IN AMYLOID ANGIOPATHY

(75) Inventors: David M. Stern, Great Neck, NY (US); Ann Marie Schmidt, Franklin Lakes, NJ (US); Shi Du Yan, New York, NY (US); Berislav Zlokovic, Rochester, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 138 days.

(21) Appl. No.: 09/638,648

(22) Filed: Aug. 14, 2000

(51) Int. Cl.$^7$ .................. A01N 61/00; A01N 37/18; A01N 43/04; G01N 33/00; C07K 17/00

(52) U.S. Cl. .................. 514/1; 514/2; 514/44; 800/3; 530/387.1

(58) Field of Search .................. 514/1, 2, 44; 800/3, 800/8, 9, 11, 13, 18, 21, 22, 25; 530/387.1; 435/455, 463, 320.1, 325

(56) References Cited

U.S. PATENT DOCUMENTS 5,864,018 A   1/1999   Morser et al. ........... 530/387.1

FOREIGN PATENT DOCUMENTS

| WO | WO 9726913 | 7/1997 |
| WO | WO-9739121 | * 10/1997 |
| WO | WO 9739125 | 10/1997 |

OTHER PUBLICATIONS

Ali et al. Neurobio. Of Aging, 17:223–234, 1996.*
Kappel et al.; Regulating gene expression in transgenic animals, 1992, Current Opinion in Biotechnology 3: 548–553.*
Strojek et al.; The Use of Transgenic Animal Techniques for Livestock Improvement, 1988, Genetic Engineering: Principles and Methods vol. 10:221–246.*
Wall; Transgenic Livestock: Progress and Prospects for the Future, 1996, Theriogenology 45: 57–68.*
Houdebine; Production of pharmaceutical proteins from transgenic animals, 1994, Journal of Biotechnology 34: 269–287.*
Hammer et. al.; Genetic Engineering of Mammalian Embryos, 1986 J. Anim. Sci. 63: 269–278.*
Ebert et. al.; A Moloney MLV–Rat Somatrotropin Fusion Gene Produces Biologically Active Somatotropin in a Transgenic Pig, 1988, Molecular Endocrinology:277–283.*
Mullins et. al.; Perspective Series: Molecular Medicine in Genetically Engineered Animals, 1996, J. Clin. Invest. vol. 98, No. 11: S37–S40.*
Stern, D., AM Schmidt and Jun Wu—A Method for Treating Symptoms Of Diabetes In A Subject (PCT/US97/21197, filed Nov. 12, 1997).

Stern, D., Shi Du Yan, Ann Marie Schmidt—PCT International Application No. PCT/US98/21346; filed Oct. 9, 1998; Ligand Binding Site of RAGE.
Stern, D., Yan, S–D. and Schmidt, A. M., U.S. patent application Ser. No. 09/374,213, filed Aug. 13, 1999, A Method of Preventing Amyloid Disturbance of Cellular Properties and for Clearing Amyloid from Tissue.
Ghersi–Egea JF, Gorevic PD, Ghiso J, Frangione BF, Patlak CS, Fenstermacher JD. Fate of cerebrospinal fluid–borne amyloid β–peptide: rapid clearance into blood and appreciable accumulation by cerebral arteries J Neurochem 1996; 67:880–83.
Hofmann MA, Drury S, Fu C, Qu W, Taguchi A, Lu Y, Avila C, Kambham N, Bierhaus A, Nawroth P, Neurath MF, Slattery T, Beach D, McClary J, Nagashima M, Morser J, Stern D, Schmidt AM. RAGE mediates a novel proinflammatory axis: a central cell surface receptor for S100/calgranulin polypeptides. Cell 1999;97:889–901.
Holtzman DM, Bales KR, Wu S, Bhat P, Parsadanian M, Fagan Am, Chang LK, Sun Y, Paul SM. In Vivo expression of apolipoprotein E Reduces amyloid–â–deposition in a mouse model of Alzheimer's Disease. J. Clin Invest 1999; 103:R15–21.
Mackic JB, Weiss MH, Miao W, Ghiso J, Calero M, Bading J, Frangione B, Zlokovic BV. Cerebrovascular accumulation and increased blood–brain barrier permeability to circulationg Alzheimer's amyloid–β peptide in aged squirrel monkey with cerebral amyloid angiopathy. J Neurochem 1998; 70:210–5.
Mackic JB, Stins M, McComb JG, Calero M, Ghiso J, Kim KS, Yan SD, Stern D, Schmidt AM, Frangione B, Zlokovic BV. Human blood–brain barrier receptors for Alzheimer's amyloid–β $_{1-40}$: asymmetrical binding, endocytosis and transcytosis at the apical side of brain microvascular endothelial cell monolayer. J Clin Invest 1998; 102:734–743.
Neeper, M., et al. (1992). Cloning and expression of a cell surface receptor for advanced glycosylation end products of proteins. *J. Biol. Chem.* 267: 14998–15004.

(List continued on next page.)

*Primary Examiner*—Deborah Crouch
*Assistant Examiner*—Thaian N. Ton
(74) *Attorney, Agent, or Firm*—John P. White; Cooper & Dunham LLP

(57) ABSTRACT

The present invention provides a method for decreasing cerebral vasoconstriction in a subject suffering from chronic or acute cerebral amyloid angiopathy which comprises administering to the subject an inhibitor of receptor for advanced glycation endproduct (RAGE) in an effective amount to inhibit transcytosis of amyloid β peptides across the blood-brain barrier in the subject, thereby decreasing cerebral vasoconstriction in the subject. The invention further provides for a method for ameliorating neurovascular stress in a subject which comprises administering to the subject an effective amount of an inhibitor of receptor for advanced glycation endproduct (RAGE), so as to increase cerebral blood flow in the subject, thereby ameliorating neurovascular stress in the subject.

9 Claims, No Drawings

OTHER PUBLICATIONS

Poduslo JF, Curran GL, Haggard JJ, Biere AL, Selkoe DJ. Permeability and residual plasma volume of human, Dutch variant, and rat amyloid β–protein 1–40 at the blood–brain barrier. Neurobiol Dis 1997;4(1) :27–34.

Schmidt, A–M, et al. (1992) "Isolation and characterization of binding proteins for advanced glycation endproducts from lung tissue which are present on the endothelial cell surface" *J. Biol. Chem.*, 267:14987–14997.

Schmidt AM, Hasu M, Popov D, Zhang JH, Chen J, Yan SD, Brett J, Cao R, Kuwabara K, Gostache G, Simionescu N, Simionecu M, Stern D. Receptor for advanced glycation end products (AGE) has a central role in vessel wall interactions and gene activation in response to circulating AGE proteins. Proc Natl Acad Sci USA 1994;91:8807–11.

Yan SD, Chen X, Fu J, Chen M, Zhu H, Roher A, Slattery T, Zhao L, Nagashima M, Morser J, Migheli A, Nawroth P, Stern D, Schmmidt AM. RAGE and amyloid–β peptide neurotoxicity in Alzheimer's disease. Nature 1996;382:685–91.

Yan SD, Zhu H, Zhu A, Golabek A, Du H, Roher A, Yu J, Soto C, Schmidt AM, Stern D, Kindy M. Receptor–dependent cell stress and amyloid accumulation in systemic amyloidosis. Nat Med 2000;6:643–51.

Zlokovic BV, et al. Clearance of amyloid–b–peptide from brain: transport or metabolism? Nature Med. 6(7), 718–719.

Zlokovic BV. Cerebrovascular permeability to peptides: manipulations of transport systems at the blood–brain barrier. Pharm Res 1995; 12 (10); 1395–1406.

* cited by examiner

METHOD TO INCREASE CEREBRAL BLOOD FLOW IN AMYLOID ANGIOPATHY

The invention disclosed herein was made with Government support under Grant No. POLAG16233 from the National Institutes of Health of the U.S. Department of Public Health. Accordingly, the U.S. Government has certain rights in this invention.

BACKGROUND OF THE INVENTION

Throughout this application, various publications are referenced by number. Full citations for these publications may be found listed at the end of the specification immediately preceding the claims. The disclosures of these publications in their entireties are hereby incorporated by reference into this application in order to more fully describe the state of the art as known to those skilled therein as of the date of the invention described and claimed herein.

The pain of Alzheimer's disease results directly from the memory loss and cognitive deficits suffered by the patient. These eventually result in the patient's loss of identity, autonomy, and freedom. As a step toward curing this disease, alleviating its symptoms, or retarding its progression, it would be desirable to develop a transgenic animal model exhibiting the main debilitating phenotype of Alzheimer's disease, that is, memory loss, expressed concomitantly with the neuropathological correlates of Alzheimer's disease, for example, beta-amyloid accumulation, increased glial reactivity, and hippocampal cell loss.

It is estimated that over 5% of the U.S. population over 65 and over 15% of the U.S. population over 85 are beset with some form of Alzheimer's disease (Cross, A. J., Eur J Pharmacol (1982) 82:77–80; Terry, R. D., et al., Ann Neurol (1983) 14:497506). It is believed that the principal cause for confinement of the elderly in long term care facilities is due to this disease, and approximately 65% of those dying in skilled nursing facilities suffer from it.

Certain facts about the biochemical and metabolic phenomena associated with the presence of Alzheimer's disease are known. Two morphological and histopathological changes noted in Alzheimer's disease brains are neurofibrillary tangles (NFT) and amyloid deposits. Intraneuronal neurofibrillary tangles are present in other degenerative diseases as well, but the presence of amyloid deposits both in the interneuronal spaces (neuritic plaques) and in the surrounding microvasculature (vascular plaques) seems to be characteristic of Alzheimer's. Of these, the neuritic plaques seem to be the most prevalent (Price, D. L., et al., Drug Development Research (1985) 5:59–68). Plaques are also seen in the brains of aged Down's Syndrome patients who develop Alzheimer's disease.

SUMMARY OF THE INVENTION

The present invention provides a method for decreasing cerebral vasoconstriction in a subject suffering from chronic or acute cerebral amyloid angiopathy which comprises administering to the subject an inhibitor of receptor for advanced glycation endproduct (RAGE) in an effective amount to inhibit transcytosis of amyloid β peptides across the blood-brain barrier in the subject, thereby decreasing cerebral vasoconstriction in the subject. The invention further provides for a method for ameliorating neurovascular stress in a subject which comprises administering to the subject an effective amount of an inhibitor of receptor for advanced glycation endproduct (RAGE), so as to increase cerebral blood flow in the subject, thereby ameliorating neurovascular stress in the subject.

DETAILED DESCRIPTION OF THE INVENTION

This invention provides for a method for decreasing cerebral vasoconstriction in a subject suffering from chronic or acute cerebral amyloid angiopathy which comprises administering to the subject an inhibitor of receptor for advanced glycation endproduct (RAGE) in an effective amount to inhibit transcytosis of amyloid β peptides across the blood-brain barrier in the subject, thereby decreasing cerebral vasoconstriction in the subject.

In one embodiment of the invention, the subject is a transgenic non-human animal or a human. In another embodiment of the invention, the non-human animal is a transgenic mouse which over-expresses mutant human amyloid beta precursor protein. In another embodiment of the invention, the subject suffers from Alzheimer's disease. In another embodiment of the invention, the chronic cerebral amyloid angiopathy is due to Alzheimer's disease, Down's syndrome, aging or angiopathy. In another embodiment of the invention, the acute cerebral amyloid angiopathy is due to head trauma, or stroke.

In one embodiment of the invention, the inhibitor is a molecule having a molecular weight from about 500 daltons to about 100 kilodaltons. In another embodiment of the invention, the inhibitor is an organic molecule or an inorganic molecule. In another embodiment of the invention, the inhibitor is a polypeptide or a nucleic acid molecule. In another embodiment of the invention, the inhibitor is soluble receptor for advanced glycation endproduct. In another embodiment of the invention, the inhibitor is an antibody which specifically binds to receptor for advanced glycation endproduct.

The invention also provides for a method for ameliorating neurovascular stress in a subject which comprises administering to the subject an effective amount of an inhibitor of receptor for advanced glycation endproduct (RAGE), so as to increase cerebral blood flow in the subject, thereby ameliorating neurovascular stress in the subject.

In one embodiment of the invention, the inhibitor of receptor for advanced glycation endproduct (RAGE) is soluble receptor for advanced glycation endproduct (RAGE). In another embodiment of the invention, the neurovascular stress comprises cerebral amyloid angiopathy. In another embodiment of the invention, the neurovascular stress in the subject is caused by Alzheimer's disease, aging, Down's syndrome, head trauma, or stroke.

The invention also provides for a method for treating amyloid angiopathy in a subject who suffers therefrom which comprises administering to the subject an effective amount of an inhibitor of receptor for advanced glycation endproduct (RAGE) activity so as to increase cerebral blood flow in the subject and thereby treat amyloid angiopathy in the subject.

The present invention provides for a method for determining whether a compound increases cerebral blood flow in a subject which comprises: (a) administering the compound to a non-human animal which exhibits at least one of the following characteristics: a correlative memory deficit, elevation of amyloid β in the brain of the non-human animal, or amyloid β plaques in the brain of the non-human animal; (b) determining whether the non-human animal has increased cerebral blood flow when compared to cerebral blood flow in an identical non-human animal which was not administered the test compound; wherein an increase in cerebral blood flow indicates that the test compound increases cerebral blood flow in a subject.

In one embodiment of the invention, the non-human animal is a transgenic non-human animal. In another embodiment of the invention, the non-human animal is a transgenic mouse which over-expresses mutant human amyloid beta precursor protein.

In another embodiment of the invention, the non-human animal is a transgenic non-human animal which is an animal model for Alzheimer's disease.

In one embodiment of the invention, the non-human animal is a Swiss transgenic mouse designated Tg APP sw+/−.

4. In one embodiment of the invention, the compound is a molecule having a molecular weight from about 500 daltons to about 100 kilodaltons. In one embodiment of the invention, the compound is an organic molecule or an inorganic molecule. In one embodiment of the invention, the compound is a polypeptide or a nucleic acid molecule.

The invention also provides for a method for ameliorating neurovascular stress in a subject which comprises administering to the subject an effective amount of an inhibitor of RAGE, so as to increase cerebral blood flow in the subject, thereby ameliorating neurovascular stress in the subject.

In one embodiment of the invention, the inhibitor of RAGE is soluble RAGE. In another embodiment of the invention, the neurovascular stress comprises amyloid angiopathy. In another embodiment of the invention, the neurovascular stress is caused by Alzheimer's disease or aging of the subject.

The invention also provides for a method for treating amyloid angiopathy in a subject who suffers therefrom which comprises administering to the subject an effective amount of an inhibitor of receptor for advanced glycation endproduct (RAGE) activity so as to increase cerebral blood flow in the subject and thereby treat amyloid angiopathy in the subject.

The invention also provides for a method for treating cerebral amyloid angiopathy in a subject who suffers therefrom which comprises administering to the subject an effective amount of a compound determined to inhibit activity of receptor for advanced glycation endproducts (RAGE) in the method described hereinabove for determining whether a compound increases cerebral blood flow in a subject.

Definitions

"DNA sequence" is a linear sequence comprised of any combination of the four DNA monomers, i.e., nucleotides of adenine, guanine, cytosine and thymine, which codes for genetic information, such as a code for an amino acid, a promoter, a control or a gene product. A specific DNA sequence is one which has a known specific function, e.g., codes for a particular polypeptide, a particular genetic trait or affects the expression of a particular phenotype.

"Genotype" is the genetic constitution of an organism.

"Phenotype" is a collection of morphological, physiological and biochemical traits possessed by a cell or organism that results from the interaction of the genotype and the environment.

"Phenotypic expression" is the expression of the code of a DNA sequence or sequences which results in the production of a product, e.g., a polypeptide or protein, or alters the expression of the zygote's or the organisms natural phenotype.

"Zygote" is a diploid cell having the potential for development into a complete organism. The zygote can result from parthenogenesis, nuclear transplantation, the merger of two gametes by artificial or natural fertilization or any other method which creates a diploid cell having the potential for development into a complete organism. The origin of the zygote can be from either the plant or animal kingdom.

In the practice of any of the methods of the invention or preparation of any of the pharmaceutical compositions an "therapeutically effective amount" is an amount which is capable of alleviating the symptoms of the disorder of memory or learning in the subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

By "nervous system-specific" is meant that expression of a nucleic acid sequence occurs substantially in a nervous system tissue (for example, the brain or spinal cord). Preferably, the expression of the nucleic acid sequence in the nervous system tissue represents at least a 5-fold, more preferably, a 10-fold, and, most preferably, a 100-fold increase over expression in non-nervous system tissue.

The "non-human animals" of the invention include vertebrates such as rodents, non-human primates, sheep, dog, cow, amphibians, reptiles, etc. Preferred non-human animals are selected from the rodent family including rat and mouse, most preferably mouse.

The "transgenic non-human animals" of the invention are produced by introducing "transgenes" into the germline of the non-human animal.

Nucleotide and Amino Acid Sequences of RAGE

The nucleotide and protein (amino acid) sequences for RAGE (both human and murine and bovine) are known. The following references which recite these sequences are incorporated by reference:

Schmidt et al, J. Biol. Chem., 267:14987–97, 1992
Neeper et al, J. Biol. Chem., 267:14998–15004, 1992

RAGE sequences (DNA sequence and translation) from bovine, murine and *homo sapien* are listed hereinbelow. These sequences are available from GenBank as are other sequences of RAGE from other species:

LOCUS BOVRAGE 1426 bp mRNA MAM 09-Dec.-1993
  DEFINITION Cow receptor for advanced glycosylation end products (RAGE) mRNA, complete cds.
ACCESSION M91212 VERSION M91212.1 GI:163650
KEYWORDS RAGE; cell surface receptor.
SOURCE Bos taurus cDNA to mRNA. ORGANISM Bos taurus Eukaryota; Metazoa; Chordata; Craniata; Vertebrata; Euteleostomi; Mammalia; Eutheria; Cetartiodactyla; Ruminantia; Pecora; Bovoidea; Bovidae; Bovinae; Bos.
REFERENCE 1 (bases 1 to 1426) AUTHORS Neeper, M., Schmidt, A. M., Brett, J., Yan, S. D., Wang, F., Pan, Y. C., Elliston, K., Stern, D. and Shaw, A. TITLE Cloning and expression of a cell surface receptor for advanced glycosylation end products of proteins
JOURNAL J. Biol. Chem. 267, 14998–15004 (1992)
MEDLINE 92340547 REFERENCE 2 (bases 1 to 1426) AUTHORS Shaw, A. TITLE Direct Submission JOURNAL Submitted (15-APR-1992) A. Shaw, Department of Cellular and Molecular Biology, Merck Sharp and Dohme Research Laboratories, West Point, Pa. 19486
USAFEATURES Location/Qualifiers source 1.1426/organism="Bos taurus"/db_xref="taxon:9913"/tissue_type="lung" CDS 10 . . . 1260/standard_name="RAGE"/codon_start=1/product="receptor for advanced glycosylation end products"/protein_id="AAA03575.1"/db_xref="GI:163651"/translation="

```
MAAGAVVGAWMLVLSLGGTVTGDQNITARIGKPLVLNCKGAPKK              (SEQ ID NO:1)
PPQQLEWKLNTGRTEAWKVLSPQGDPWDSVARVLPNGSLLLPAVGIQDEGTFRCRATS
RSGKETKSNYRVRVYQIPGKPEIVDPASELMAGVPNKVGTCVSEGGYPAGTLNWLLDG
KTLIPDGKGVSVKEETKRHPKTGLFTLHSELMVTPARGGALHPTFSCSFTPGLPRRRA
LHTAPIQLRVWSEHRGGEGPNVDAVPLKEVQLVVEPEGGAVAPGGTVTLTCEAPAQPP
PQIHWIKDGRPLPLPPGPMLLLPEVGPEDQGTYSCVATHPSHGPQESRAVSVTIIETG
EEGTTAGSVEGPGLETLALTLGILGGLGTVALLIGVIVWHRRRQRKGQERKVPENQEE
EEEERAELNQPEEPEAAESSTGGP
``` polyA_signal 1406 . . . 1411 polyA_site 1426
BASE COUNT 322 a 429 c 440 g 235 t

```
ORIGIN
1    cggagaagga tggcagcagg ggcagtggtc ggagcctgga tgctagtcct   (SEQ ID NO:2)
cagtctgggg 61 gggacagtca cgggggacca aaacatcaca gcccggatcg
ggaagccact ggtgctgaac 121 tgcaagggag ccccaagaa accaccccag
cagctggaat ggaaactgaa cacaggccgg 181 acagaagctt ggaaagtcct
gtctccccag ggagacccct gggatagcgt ggctcgggtc 241 ctccccaacg
gctccctcct cctgccggct gttgggatcc aggatgaggg gactttccgg 301
tgccgggcaa cgaccggag cggaaaggag accaagtcta actaccgagt
ccgagtctat 361 cagattcctg gaagccaga aattgttgat cctgcctctg
aactcatggc tggtgtcccc 421 aataaggtgg ggacatgtgt gtccgagggg
ggctaccctg cagggactct taactggctc 481 ttggatggga aaactctgat
tcctgatggc aaaggagtgt cagtgaagga agagaccaag 541 agacacccaa
agacagggct tttcacgctc cattcggagc tgatggtgac cccagctcgg 601
ggaggagctc tccacccac cttctcctgt agcttcaccc ctggccttcc
ccggcgccga 661 gccctgcaca cggcccccat ccagctcagg gtctggagtg
agcaccgagg tggggagggc 721 cccaacgtgg acgctgtgcc actgaaggaa
gtccagttgg tggtagagcc agaagggga 781 gcagtagctc ctggtggtac
tgtgaccttg acctgtgaag ccccgccca gccccacct 841 caaatccact
ggatcaagga tggcaggccc ctgcccttc ccctggccc catgctgctc 901
ctcccagagg tagggcctga ggaccaggga acctacagtt gtgtggccac
ccatcccagc 961 catgggcccc aggagagccg tgctgtcagc gtcacgatca
tcgaaacagg cgaggagggg 1021 acgactgcag gctctgtgga agggccgggg
ctggaaaccc tagccctgac cctggggatc 1081 ctggaggcc tggggacagt
cgccctgctc attggggtca tcgtgtggca tcgaaggcgg 1141 caacgcaaag
gacaggagag gaaggtcccg gaaaaccagg aggaggaaga ggaggagaga 1201
gcggaactga accagccaga ggagcccgag gcggcagaga gcagcacagg
agggcctga 1261 ggagcccacg gccagacccg atccatcagc ccctttctct
```

-continued

```
ttcccacact ctgttctggc 1321 cccagaccag ttctcctctg tataatctcc agcccacatc tcccaaactt tcttccacaa 1381 ccagagcctc ccacaaaaag tgatgagtaa acacctgcca cattta//
```

LOCUS HUMRAGE 1391 bp mRNA PRI 09-Dec.-1993
DEFINITION Human receptor for advanced glycosylation end products (RAGE) mRNA, partial cds.
ACCESSION M91211 VERSION M91211.1 GI:190845
KEYWORDS RAGE; cell surface receptor.
SOURCE *Homo sapiens* cDNA to mRNA.
ORGANISM *Homo sapiens* Eukaryota; Metazoa; Chordata; Craniata; Vertebrata; Euteleostomi; Mammalia; Eutheria; Primates; Catarrhini; Hominidae; Homo.
REFERENCE 1 (bases 1 to 1391)
AUTHORS Neeper, M., Schmidt, A. M., Brett, J., Yan, S. D., Wang F., Pan, Y. C., Elliston, K., Stern, D. and Shaw, A.
TITLE Cloning and expression of a cell surface receptor for advanced glycosylation end products of proteins
JOURNAL J. Biol. Chem. 267, 14998–15004 (1992)
MEDLINE 92340547
REFERENCE 2 (bases 1 to 1391)
AUTHORS Shaw, A.
TITLE Direct Submission
JOURNAL Submitted (15-APR-1992) A. Shaw, Department of Cellular and Molecular Biology, Merck Sharp and Dohme Research Laboratories, West Point, Pa. 19486 USA
FEATURES Location/Qualifiers source 1 . . . 1391/ organism="*Homo sapiens*"/db_xref="taxon:9606"/ tissue_type="lung" CDS <1 . . . 1215/standard_name= "RAGE"/codon_start=1/product="receptor for advanced glycosylation end products"/protein_id="AAA03574.1"/ db_xref="GI:190846"/translation="

```
           GAAGTAVGAWVLVLSLWGAVVGAQNITARIGEPLVLKCKGAPKK                    (SEQ ID NO:3)

PPQRLEWKLNTGRTEAWKVLSPQGGGPWDSVARVLPNGSLFLPAVGIQDEGIFRCRAM

NRNGKETKSNYRVRVYQIPGKPEIVDSASELTAGVPNKVGTCVSEGSYPAGTLSWHLD

GKPLVPNEKGVSVKEQTRRHPETGLFTLQSELMVTPARGGDPRPTFSCSFSPGLPRHR

ALRTAPIQPRVWEPVPLEEVQLVVEPEGGAVAPGGTVTLTCEVPAQPSPQIHWMKDGV

PLPLPPSPVLILPEIGPQDQGTYSCVATHSSHGPQESRAVSISIIEPGEEGPTAGSVG

GSGLGTLALALGILGGLGTAALLIGVILWQRRQRRGEERKAPENQEEEEERAELNQSE

EPEAGESSTGGP
``` polyA_signal 1368 . . . 1373 polyA_site 1391
BASE COUNT 305 a 407 c 418 g 261 t

```
ORIGIN
    1 ggggagccg aacagcagt tggagcctgg gtgctggtcc tcagtctgtg gggggcagta  (SEQ ID NO:4)

61 gtaggtgctc aaaacatcac agcccggatt ggcgagccac tggtgctgaa gtgtaagggg 121 gcccccaaga aaccaccca gcggctgaa tggaaactga acacaggccg gacagaagct 181 tggaaggtcc tgtctcccca gggaggaggc ccctgggaca gtgtggctcg tgtccttccc 241 aacggctccc tcttccttcc ggctgtcggg atccaggatg aggggatttt ccggtgcagg 301 gcaatgaaca ggaatggaaa ggagaccaag tccaactacc gagtccgtgt ctaccagatt 361 cctgggaagc cagaaattgt agattctgcc tctgaactca cggctggtgt tcccaataag 421 gtggggacat gtgtgtcaga gggaagctac cctgcaggga ctcttagctg gcacttggat 481 gggaagcccc tggtgcctaa tgagaaggga gtatctgtga aggaacagac caggagacac 541 cctgagacag ggctcttcac actgcagtcg gagctaatgg tgaccccagc ccggggagga 601 gatcccgtc ccaccttctc ctgtagcttc agcccaggcc ttccccgaca ccgggccttg 661 cgcacagccc ccatccagcc ccgtgtctgg gagcctgtgc ctctggagga ggtccaattg 721 gtggtggagc cagaaggtgg agcagtagct cctggtggaa ccgtaaccct gacctgtgaa
```

-continued

```
 781 gtccctgccc agccctctcc tcaaatccac tggatgaagg atggtgtgcc cttgcccctt 841 cccccagcc ctgtgctgat cctccctgag atagggcctc aggaccaggg aacctacagc 901 tgtgtggcca cccattccag ccacgggccc caggaaagcc gtgctgtcag catcagcatc 961 atcgaaccag gcgaggaggg gccaactgca ggctctgtgg gaggatcagg gctgggaact 1021 ctagccctgg ccctggggat cctgggaggc ctggggacag ccgccctgct cattggggtc 1081 atcttgtggc aaaggcggca acgccgagga gaggagagga aggccccaga aaaccaggag 1141 gaagaggagg agcgtgcaga actgaatcag tcggaggaac ctgaggcagg cgagagtagt 1201 actggagggc cttgagggcc ccacagacag atcccatcca tcagctccct tttcttttc 1261 ccttgaactg ttctggcctc agaccaactc tctcctgtat aatctctctc ctgtataacc 1321 ccaccttgcc aagctttctt ctacaaccag agccccccac aatgatgatt aaacacctga 1381 cacatcttgc a//
```

LOCUS MUSRECEP 1348 bp mRNA ROD 23-AUG-1994
DEFINITION Mouse receptor for advanced glycosylation end products (RAGE) gene, complete cds.
ACCESSION L33412 VERSION L33412.1 GI:532208
KEYWORDS receptor for advanced glycosylation end products.
SOURCE Mus musculus (strain BALB/c, sub_species domesticus) (library: lambda gt10) male adult lung cDNA to mRNA.
ORGANISM Mus musculus Eukaryota; Metazoa; Chordata; Craniata; Vertebrata; Euteleostomi; Mammalia; Eutheria; Rodentia; Sciurognathi; Muridae; Murinae; Mus.
REFERENCE 1 (bases 1 to 1348)
AUTHORS Lundh, E. R., Morser, J., McClary, J. and Nagashima, M.
TITLE Isolation and characterization of cDNA encoding the murine and rat homologues of the mammalian receptor for advanced glycosylation end products
JOURNAL Unpublished COMMENT On Aug. 24, 1994 this sequence version replaced gi:496146.
FEATURES Location/Qualifiers source 1 . . . 1348/ organism="Mus musculus"/strain="BALB/c"/sub_species="domesticus"/db_xref="taxon:10090"/sex="male"/tissue_type="lung"/dev_stage="adult"/tissue_lib="lambda gt10" gene 6 . . . 1217/gene="RAGE" CDS 6 . . . 1217/gene="RAGE"/codon_start=1/product="receptor for advanced glycosylation end products"/protein_id="AAA40040.1"/db_xref—"GI:532209"/translation="

MPAGTAARAWVLVLALWGAVAGGQNITARIGEPLVLSCKGAPKK    (SEQ ID NO:5)

PPQQLEWKLNTGRTEAWKVLSPQGGPWDSVAQILPNGSLLLPATGIVDEGTFRCRATN

RRGKEVKSNYRVRVYQIPGKPEIVDPASELTASVPNKVGTCVSEGSYPAGTLSWHLDG

KLLIPDGKETLVKEETRRHPETGLFTLRSELTVIPTQGGTTHPTFSCSFSLGLPRRRP

LNTAPIQLRVREPGPPEGIQLLVEPEGGIVAPGGTVTLTCAISAQPPPQVHWIKDGAP

LPLAPSPVLLLPEVGHADEGTYSCVATHPSHGPQESPPVSIRVTETGDEGPAEGSVGE

SGLGTLALALGILGGLGVVALLVGAILWRKRQPRREERKAPESQEDEEERAELNQSEE

AEMPENGAGGP polyA_site 1333
BASE COUNT 301 a 394 c 404 g 249 t

```
ORIGIN
    1 gcaccatgcc agcggggaca gcagctagag cctgggtgct ggttcttgct ctatggggag   (SEQ ID NO:6)
   61 ctgtagctgg tggtcagaac atcacagccc ggattggaga gccacttgtg ctaagctgta
  121 aggggccccc taagaagccg ccccagcagc tagaatggaa actgaacaca ggaagaactg
  181 aagcttggaa ggtcctctct ccccaggag gcccctggga cagcgtggct caaatcctcc
  241 ccaatggttc cctcctcctt ccagccactg gaattgtcga tgaggggacg ttccggtgtc
  301 gggcaactaa caggcgaggg aaggaggtca agtccaacta ccgagtccga gtctaccaga
  361 ttcctgggaa gccagaaatt gtggatcctg cctctgaact cacagccagt gtccctaata
  421 aggtggggac atgtgtgtct gagggaagct accctgcagg gacccttagc tggcacttag
  481 atgggaaact tctgattccc gatggcaaag aaacactcgt gaaggaagag accaggagac
  541 accctgagac gggactcttt acactgcggt cagagctgac agtgatcccc acccaaggag
  601 gaaccaccca tcctaccttc tcctgcagtt tcagcctggg ccttcccgg cgcagacccc
  661 tgaacacagc ccctatccaa ctccgagtca gggagcctgg gcctccagag ggcattcagc
  721 tgttggttga gcctgaaggt ggaatagtcg ctcctggtgg gactgtgacc ttgacctgtg
  781 ccatctctgc ccagcccct cctcaggtcc actggataaa ggatggtgca cccttgcccc
  841 tggctcccag ccctgtgctg ctcctccctg aggtggggca cgcggatgag ggcacctata
  901 gctgcgtggc cacccaccct agccacggac ctcaggaaag ccctcctgtc agcatcaggg
  961 tcacagaaac cggcgatgag gggccagctg aaggctctgt gggtgagtct gggctgggta
 1021 cgctagccct ggccttgggg atcctgggag gcctgggagt agtagccctg ctcgtcgggg
 1081 ctatcctgtg gcgaaaacga caacccaggc gtgaggagag gaaggcccg gaaagccagg
 1141 aggatgagga ggaacgtgca gagctgaatc agtcagagga agcggagatg ccagagaatg
 1201 gtgccggggg accgtaagag cacccagatc gagcctgtgt gatggcccta gagcagctcc
 1261 cccacattcc atcccaattc ctccttgagg cacttccttc tccaaccaga gcccacatga
 1321 tccatgctga gtaaacattt gatacggc//
```

Inhibitors of RAGE:

Inhibitors of RAGE include any molecule which, when introduced into a cell or a subject, is capable of inhibiting the biological activity of RAGE. For example, one such inhibitor would be able to inhibit the activity of RAGE as described: the activity of transcytosis of amyloid beta peptides across the blood brain barrier within a subject.

Examples of an inhibitor of RAGE activity are soluble RAGE, an antibody which specifically binds to RAGE, a truncated version of RAGE which is capable of acting as a competitive inhibitor of RAGE. A fragment of RAGE which includes the amyloid beta peptide binding portion of RAGE and introduced into the cell or subject as a soluble polypeptide. Other types of inhibitors would be known to one of skill in the art. For example, a small molecule could be prepared which mimics the amyloid beta peptide binding region of RAGE and administered alone as an inhibitor.

Pharmaceutical Compositions and Carriers

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of protein compositions and compounds together with suitable diluents, preservatives, solubilizers, emulsifiers, adjuvants and/or carriers useful in treatment of neuronal degradation due to aging, a learning disability, or a neurological disorder. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the compound of the invention may be "labeled" by association with a detectable marker substance (e.g., radiolabeled with $^{125}I$ or biotinylated) to provide reagents useful in detection and quantification of compound or its receptor bearing cells or its derivatives in solid tissue and fluid samples such as blood, cerebral spinal fluid or urine.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents in containing amino hydrazine or hydrazide groups are useful for reaction with aldehydes generated by periodate oxidation of carbohydrate groups in proteins.

In one embodiment the compound of the present invention is associated with a pharmaceutical carrier which includes a pharmaceutical composition. The pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

Transgenic Technology and Methods

The following U.S. Patents are hereby incorporated by reference: U.S. Pat. No. 6,025,539, IL-5 transgenic mouse; U.S. Pat. No. 6,023,010, Transgenic non-human animals depleted in a mature lymphocytic cell-type; U.S. Pat. No. 6,018,098, In vivo and in vitro model of cutaneous photoaging; U.S. Pat. No. 6,018,097, Transgenic mice expressing human insulin; U.S. Pat. No. 6,008,434, Growth differentiation factor-11 transgenic mice; U.S. Pat. No. 6,002,066; H2-M modified transgenic mice; U.S. Pat. No. 5,994,618, Growth differentiation factor-8 transgenic mice; U.S. Pat. No. 5,986,171, Method for examining neurovirulence of polio virus, U.S. Pat. No. 5,981,830, Knockout mice and their progeny with a disrupted hepsin gene; U.S. Pat. No. 5,981,829, .DELTA.Nur77 transgenic mouse; U.S. Pat. No. 5,936,138; Gene encoding mutant L3T4 protein which facilitates HIV infection and transgenic mouse expressing such protein; U.S. Pat. No. 5,912,411, Mice transgenic for a tetracycline-inducible transcriptional activator; U.S. Pat. No. 5,894,078, Transgenic mouse expressing C-100 app.

The methods used for generating transgenic mice are well known to one of skill in the art. For example, one may use the manual entitled "Manipulating the Mouse Embryo" by Brigid Hogan et al. (Ed. Cold Spring Harbor Laboratory) 1986.

See for example, Leder and Stewart, U.S. Pat. No. 4,736,866 for methods for the production of a transgenic mouse.

For sometime it has been known that it is possible to carry out the genetic transformation of a zygote (and the embryo and mature organism which result therefrom) by the placing or insertion of exogenous genetic material into the nucleus of the zygote or to any nucleic genetic material which ultimately forms a part of the nucleus of the zygote. The genotype of the zygote and the organism which results from a zygote will include the genotype of the exogenous genetic material. Additionally, the inclusion of exogenous genetic material in the zygote will result in a phenotype expression of the exogenous genetic material.

The genotype of the exogenous genetic material is expressed upon the cellular division of the zygote. However, the phenotype expression, e.g., the production of a protein product or products of the exogenous genetic material, or alterations of the zygote's or organism's natural phenotype, will occur at that point of the zygote's or organism's development during which the particular exogenous genetic material is active. Alterations of the expression of the phenotype include an enhancement or diminution in the expression of a phenotype or an alteration in the promotion and/or control of a phenotype, including the addition of a new promoter and/or controller or supplementation of an existing promoter and/or controller of the phenotype.

The genetic transformation of various types of organisms is disclosed and described in detail in U.S. Pat. No. 4,873, 191, issued Oct. 10, 1989, which is incorporated herein by reference to disclose methods of producing transgenic organisms. The genetic transformation of organisms can be used as an in vivo analysis of gene expression during differentiation and in the elimination or diminution of genetic diseases by either gene therapy or by using a transgenic non-human mammal as a model system of a human disease. This model system can be used to test putative drugs for their potential therapeutic value in humans.

The exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote. The zygote is allowed to develop into an organism such as by implanting it in a pseudopregnant female. The resulting organism is analyzed for the integration of the exogenous genetic material. If positive integration is determined, the organism can be used for the in vivo analysis of the gene expression, which expression is believed to be related to a particular genetic disease.

Attempts have been made to study a number of different types of genetic diseases utilizing such transgenic animals. Attempts related to studying Alzheimer's disease are disclosed within published PCT application WO89/06689 and PCT application WO89/06693, both published on Jul. 27, 1989, which published applications are incorporated herein by reference to disclose genetic sequences coding for Alzheimer's .beta.-amyloid protein and the incorporation of such sequences into the genome of transgenic animals.

Embryonal target cells at various developmental stages can be used to introduce transgenes. Different methods are used depending on the stage of development of the embryonal target cell. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al. (1985) Proc. Natl. Acad. Sci. U.S.A. 82, 4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) Proc. Natl. Acad. Sci U.S.A. 73, 1260–1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al. (1985) Proc. Natl. Acad. Sci. U.S.A. 82, 6927–6931; Van der Putten, et al. (1985) Proc. Natl. Acad. Sci U.S.A. 82, 6148–6152). Transfection is easily and efficiently obtained by culturing the blastomeres on a monolayer of virus-producing cells (Van der Putten, supra; Stewart, et al. (1987) EMBO J. 6, 383–388). Alternatively, infection can be performed at a later stage. Virus or virus-producing cells can be injected into the blastocoele (Jahner, D., et al. (1982) Nature 298, 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, D. et al. (1982) supra).

A third type of target cell for transgene introduction is the embryonal stem cell (ES). ES cells are obtained from pre-implantation embryos cultured in vitro and fused with embryos (Evans, M. J., et al. (1981) Nature 292, 154–156; Bradley, M. O., et al. (1984) Nature 309, 255–258; Gossler, et al. (1986) Proc. Natl. Acad. Sci U.S.A. 83, 9065–9069; and Robertson, et al. (1986) Nature 322, 445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240, 1468–1474.

As used herein, a "transgene" is a DNA sequence introduced into the germline of a non-human animal by way of human intervention such as by way of the above described methods.

The disclosures of publications referenced in this application in their entireties are hereby incorporated by reference into this application in order to more fully describe the state of the art as known to those skilled therein as of the date of the invention described and claimed herein.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Receptor for Advanced Glycation Endproduct (RAGE)-Dependent Neurovascular Dysfunction Caused by Amyloid-β Peptide Amyloid-beta peptides (Aβ) are important in the pathogenesis of Alzheimer's dementia. We show that RAGE mediates Aβ transport across the blood-brain barrier (BBB) in mice followed by its rapid neuronal uptake, cytokine response, oxidant stress and reductions in the cerebral blood flow (CBF). Antagonizing RAGE in transgenic mice that overexpress mutant human Aβ precursor protein restored the CBF and ameliorated neurovascular stress. In Alzheimer's brains, vascular expression of RAGE was associated with Aβ accumulation. We suggest that RAGE at the BBB is a potential target for inhibiting vascular accumulation of AO and for limiting cellular stress and ischemic changes in Alzheimer's dementia.

Deposition of Aβ in the CNS occurs during normal aging and is accelerated by Alzheimer's Disease (AD) [1-4] Aβ is implicated in neuropathology of AD and related disorders. [1-4] Aβ peptides have neurotoxic properties in vitro [5-7] and in vivo, [8-10] and induce neuronal oxidant stress directly and indirectly by activating microglia. [11-13] Aβ generates superoxide radicals in brain endothelium, [14] and at higher concentrations may damage endothelial cells. [15] Recent studies from our and other laboratories suggest a major role of the blood-brain barrier (BBB) in determining the concentrations of Aβ in the CNS. [16-25] The BBB controls the entry of plasma-derived Aβ and its binding transport proteins into the CNS, and regulates the levels of brain-derived Aβ via clearance mechanisms.

RAGE (receptor for advanced glycation end-product), a multiligand receptor in the immunoglobulin superfamily binds free Aβ in the nanomolar range, and mediates pathophysiological cellular responses when occupied by glycated ligands, Aβ, S100/calgranulins or serum amyloid A. [24,26-28] RAGE is up-regulated on microglia and vascular endothelium in AD brains. [29,30] We have recently reported that RAGE may be involved in transport of Aβ across human brain endothelial monolayers. [24,31] Our current study demonstrates that RAGE mediates in vivo transcytosis of Aβ1–40 and Aβ1–42 across the BBB in mice. RAGE-dependent BBB transport of Aβ was coupled to its rapid neuronal uptake, induction of cellular stress and transient, but significant suppression of cerebral blood flow (CBF). Antagonizing RAGE in transgenic mice that overexpress mutant human Aβ precursor protein (APP) restored the CBF and ameliorated cellular stress. In Alzheimer's brains, vascular expression of RAGE was associated with AS accumulation. These data support the possibility that inhibiting RAGE at the BBB may limit vascular accumulation of AB and reduce cellular stress and ischemic changes in Alzheimer's dementia.

RAGE Mediates in Vivo Transcytosis of Aβ Across the BBB

RAGE-dependent binding to brain microvessels and transport across the BBB of human and mouse $A\beta_{1-40}$, and somewhat slower, but significant RAGE-dependent BBB transport of $A\beta_{1-42}$ and absence of its significant binding to microvessels were found in mice and guinea pigs. Aβ transport into brain was significantly inhibited by 65% to 85% by circulating α-RAGE IgG (5–40 μg/kg) and abolished by sRAGE. Several other molecular reagents including fucoidan (a ligand for the scavenger receptor type A), anti-β1-integrin antibodies, or RHDS peptide (5–9 sequence of Aβ) did not affect either BBB transport or binding of Aβ. Although Aβ peptides were partially metabolized during their transport across the BBB (i.e., ≦50% for 10 min), significant and rapid RAGE-dependent neuronal uptake of circulating Aβ was observed after the BBB transport.

Circulating Aβ and RAGE-Dependent Neurovascular Stress

Transport of $A\beta_{1-40}$ across the BBB was associated with an early cellular stress response that preceded changes in the CBF. The expression of TNF-α mRNA and protein on different cells in brain parenchyma, including neurons and brain endothelium was evident after 15 min of transport of circulating AS across the BBB. Treatment with circulating sRAGE or α-RAGE IgG abolished Aβ-induced TNF-α expression. Aβ transport across the BBB resulted in rapid neuronal expression of 1L-6 and HO-1, and these effects were abolished by either α-RAGE IgG or sRAGE, supporting the concept that RAGE-dependent Aβ BBB transport initiates cellular stress in brain. RAGE-dependent Aβ-induced cellular stress was found either after cerebral arterial or systemic intravenous administration of Aβ, and persisted in brain for few hours. Expression of TNF-α, IL-6 and HO-1 was observed in brain 2 hrs after i.v. administration of $A\beta_{1-40}$ at low nanomolar level.

Systemic administration of $A\beta_{1-40}$, (either human or murine) at low nanomolar concentrations resulted in time-dependent decrease in the CBF, but did not affect systemic arterial blood pressure. Reductions in the CBF were detectable after 20–30 min of AB administration, and maximal decrease in the CBF was observed between 40–60 min. CBF changes were completely antagonized by circulating α-RAGE at 40 μg/ml. Aβ-induced cerebral vasospasm was antagonized by α-RAGE in a dose-dependent manner, was abolished by sRAGE, but was not affected by an irrelevant antibody.

RAGE Blockade Restores the CBF in Tg APP sw+/−Mice

A significant decease in basal CBF values in 9 months old Tg APPsw+/−mice compared to age-matched control mice as determined by laser Doppler flowmetry, and confirmed by quantitative autoradiographic analysis. There was no difference in the arterial blood pressure between wild type and Tg APPsw+/−mice. Infusion of α-RAGE dramatically increased the CBF in Tg APPsw+/−mice, and the effect was maximal between 60–120 min after systemic administration of α-RAGE. An irrelevant IgG did not affect the CBF in Tg APPsw+/−animals. Systemic administration of α-RAGE ameliorated cellular stress in brain of 9 month old Tg APPsw+/−mice, as indicated by moderate reduction in expression of TNF-a, IL-6 and HO-1. Expression of RAGE on brain microvessels was enhanced in Tg PPsw+/−mice, and increased vascular expression of RAGE was associated with accumulation of Aβ in AD brains.

Discussion

These data demonstrate that RAGE has an important role in Aβ-mediated uptake at the BBB and its transport into the central nervous system, as well as Aβ-mediated cellular perturbation.

The first set of studies employed synthetic Aβ infused in to wild-type mice, and the results apply to acute exposure of vasculature to AS.

This invention provides the following methods:

A method for blockading RAGE, with either sRAGE or anti-RAGE IgG which thereby, suppresses binding to and uptake of Aβ in relation to the vessel wall inhibits Aβ-induced cell stress in the vasculature and in neurons, consequent to systemic infusion of Aβ

Such an experimental model, although artificial, may be directly relevant to head trauma, stroke and other disorders in which there are acute elevations of Aβ.

The second set of studies uses the Hsiao mice (reference for these is Hisao K, Chapman P, Nilsen S, Eckman C, Harigaya Y, Younkin S, Yang F, Cole G: correlative memory deficits, Aβ elevation, and amyloid plaques in transgenic mice. Science 274:99, 1996). These experiments suggests that chronic exposure of vasculature to Aβ results in RAGE-dependent vasoconstriction—thus, a RAGE blocker would be expected to increase cerebral blood flow in patients with increased levels of amyloid-beta peptide (at least when Aβ is in the blood or blood vessel wall). These mice were made using the prion promoter, which expresses amyloid precursor protein in neurons and glial cells, predominately, but some seems to get into the vasculature as well. These mice are considered a model of Alzheimer's disease. Thus, increasing cerebral blood flow in these mice could be interpreted as increasing cerebral blood flow in the setting of Alzheimer's disease. Decreased blood flow would be considered an adverse effect for cerebral function, thus, increasing blood flow would be considered (at least indirectly) neuroprotective.

The second set of studies actually is more powerful in terms of its implications since the mice are considered a model of Alzheimer's-type pathology.

Methods

Synthetic peptides: $A\beta_{1-40}$ and $A\beta_{1-42}$ human forms, and $A\beta_{1-40}$ murine form were be synthesized at the W M Keck Facility at Yale University using solid-phase tBOC(N-tert-butyloxycarbonyl)-chemistry, purified by HPLC, and the final products lyophilized and characterized by analytical reverse-phase HPLC, amino acid analysis, laser desorption mass spectrometry, as we previously described. [22,24] Stock solutions were prepared in DMSO to assure monomeric species, and kept at −80° C. until use.

Radioiodination: of Aβ was carried out with Na[$^{125}$I] and Iodobeads (Pierce), and the resulting components resolved by HPLC. [22,24]

Animals and tissue preparation: TgAPPsw+/−mice (bearing the double mutation Lys670Asn, Met671Leu) 9 months of age were in a mixed C57B6/SJL background, as were age-matched wild type control mice were used throughout the study. Animals were screened for the presence of the APP transgenes by PCR as described. [35] For histology, mice received intraperitoneal (i.p.) pentobarbital (150 mg/kg) and were perfused transcardially with 0.1M PBS (pH 7.4) at 4° C. The right hemisphere was immersion-fixed in 4% paraformaldehyde in 0.1 M phosphate buffer (pH 7.4) at 4° C. overnight. The brain was cryoprotected in 30% sucrose in PBS at 4° C., and then fixed in paraformaldehyde as above at 4° C.

Cerebral blood flow measurement: CBF was monitored by Laser Doppler Flowmetry (LDF, Transonic BLF21, NY) as we described. [36] LDF probes (0.8 mm diameter) were positioned on the cortical surface 2 mm posterior to the bregma, both 3 and 6 mm to each side of midline. The CBF was also determined by quantitative autoradiography using $^{14}$C-iodoantipryine (IAP) using recently reported modified method in the whole mouse. [37] Briefly, 0.15 μCi $^{14}$C-IAP was injected i.p. and animals sacrificed after 2 min. Blood from the frozen heart was sampled to obtain the final blood $^{14}$C-IAP level. Frozen brains were coronally sectioned at 20 μm and exposed to autoradiographic film along with radioactive $^{14}$C standards. After a 5 day exposure, the film was developed and the resulting images analyzed by quantitative autoradiography to determine levels of $^{14}$C-IAP in individual brain regions. The CBF was calculated as reported: [37,40] $F=-\lambda \ln(1-C_{IN\ (T)}/\lambda\ C_{PL})/T$, where F is the rate of flow per unit mass ($^{-1}$), $C_{IN\ (T)}$ is activity in unit weight of brain at time T, $C_{PL}$ is the concentration of $^{14}$C-IAP in the blood, and λ is the distribution ratio of $^{14}$C-IAP between brain and the perfusion medium or blood at the steady state, i.e. 0.8.

Aβ (4 nM/1) or vehicle were administered via femoral vein (n=5 per group). α-RAGE, sRAGE etc.

Brain perfusion model. This model has bee extensively used to determine peptide and protein binding to and transport across the BBB [22,23,38,39] For intra-arterial brain perfusion technique mice were anesthetized with i.p. ketamine (0.5 mg/kg) and xylazine (5 mg/kg), and the right common carotid artery isolated and connected to an extracorporeal perfusion circuit via fine polyethylene cannula (PE10). Details of the extracorporeal perfusion circuit were as reported elsewhere. [22,23,38,39] At the start of the perfusion, the contralateral common carotid artery was ligated, and both jugular veins severed to allow free drainage of the perfusate. Brains were perfused with oxygenated perfusion medium at a flow rate of 1 ml/min by peristaltic pump. The perfusion medium consisted of 20% sheep red blood cells (oxygen carrier) suspended in mock plasma containing 48 g/L dextran (FW 70 000) to maintain colloid osmotic pressure, and electrolytes and D-glucose (196 mg/dl) at concentrations corresponding to normal mouse plasma levels. Perfusion pressure and animal's own arterial blood pressure were continuously monitored. Blood gasses pO2, pCO2 and pH and electrolytes in the arterial inflow and in animal's own blood were monitored. All physiological parameters were kept within the normal range as we described. [22,23,38,39]

Injection of radioisotopes for transport studies. [$^{125}$I]-Aβ, $^{99m}$Tc-albumin or $^{14}$C-labeled inulin were infused into arterial inflow at a rate of 0.1 ml/min typically within 10 min for transport studies (corresponds to the linear phase of Aβ uptake). When the effects of different unlabeled molecular reagents were tested, those were injected 5 min prior to tracers injection and than simultaneously with radiolabled ligands. At predetermined times within 10 min mice were sacrificed by decapitation, and brain tissue prepared for radioactivity analysis. TCA and HPLC analysis as we described were used to determine molecular forms of uptake of radiolabeled Aβ by the BBB. [22,23] Capillary-depletion technique was used to separate micravascular pellet from capillary-depleted brain to quantify in vivo binding to microvessels vs. transport into brain parenchyma, as we reported. [22,23]

Mathematical modeling for transport studies. We have reported details of mathematical analysis elsewhere. [22,23,38,39] The uptake values for $^{125}$I-Aβ were based on the amount of intact molecule as determined by the TCA and HPLC analysis. The rate of entry ($K_{IN}$) is computed from eq. 1: $d[C_{IN\ (TEST-MOLECULE)}-C_{IN\ (ALBUMIN)}]/dt = K_{IN}\ C_{PL} - K_{OUT}[C_{IN\ (TEST-MOLECULE)} - C_{IN\ (ALBUMIN)}]$, where $K_{OUT}$ is exit or efflux transfer coefficient, and R is the steady state or equilibrium ratio. Eq. 1 is integrated to give $[C_{IN\ (TEST-MOLECULE)} - C_{IN\ (ALBUMIN)}]/C_{PL} = R(1-e^{-K_{OUT}T})$ (eq. 2). R is the steady state ratio, and the ratio $K_{IN}/K_{OUT}$ at infinite time, and T is infusion time. Numerical values for $K_{OUT}$ may be obtained from the slope of the plot of in $(R-[C_{IN\ (TEST-MOLECULE)} - C_{IN\ (ALBUMIN)}]/C_{PL})$ (eq. 3) against T, using the equation $K_{OUT} = -\ln(R-[C_{IN\ (TEST-MOLECULE)} - C_{IN\ (ALBUMIN)}]/C_{PL})/T$ (eq. 4). Finally, the value for $K_{IN}$ is derived by substituting the number for $K_{OUT}$ in: $K_{IN}=R\ K_{OUT}$ (eq. 5). When tracer uptake remains linear over studied period of time, the exist constant approaches zero, and $K_{IN}=d\ [C_{IN\ (TEST-MOLECULE)} - C_{IN\ (ALBUMIN)}]/dt\ C_{PL}$. The $K_{IN}$ represents the fraction of circulating radioactive ligands that is taken up intact by 1 g of brain from 1 ml of plasma in 1 min, and is the same as the PS product if $K_{IN}$ or PS <<CBF, [39] a condition satisfied by Aβ. Advanced graphics software and the MLAB mathematical modeling system (as above) will be used to obtain graphic plots and compute transfer coefficients.

Immunocytochemical analysis: for TNF-α, IL-6 and HO-1 in brains of wild type mice and TgAPPsw+/−mice was performed using standard techniques, as described (26). Briefly, fresh-frozen, acetone-fixed brain sections of wild type and TgAPPsw+/−mice were stained with anti-TNF-a IgG (Santa Cruz), anti-IL-6 IgG (Santa Cruz and anti-HO-1 IgG (StressGen) as primary antibodies. The extent and intensity of staining in cellular elements was quantitated using the Universal Imaging System and NIH imaging systems. The relative intensity of cellular staining in control brain sections was compared to treated brains. Routine control sections included deletion of primary antibody, deletion of secondary antibody and the use of an irrelevant primary antibody.

Statistical analysis. Data from the proposed studies were analyzed by multifactorial analysis of variance (ANOVA) that ranged from one-way to three-way ANOVA. Each ANOVA included an analysis of residuals as a check on the required assumptions of normally distributed errors with constant variance. In the event the required assumptions were not satisfied, data transformations were considered. Appropriate multiple comparisons were included as a part of each analysis. For pair-wise comparisons, the Tukey method was used, and for comparisons with a control group we used Dunnett's test.

Example 2

RAGE at the Blood Brain Barrier Mediates Neurovascular Dysfunction Caused by Amyloid $\beta_{1-40}$ Peptide Amyloid-beta peptides (Aβ) are important in the pathogenesis of Alzheimer's dementia. We found that the receptor for advanced glycation end products (RAGE) mediates in vivo transcytosis of cireculating $A\beta_{1-40}$ across the blood-brain barrier (BBB) in mice. In an acute model in mice, blood to brain transport of $A\beta_{1-40}$ (1–4 nM final plasma concentration) was coupled to its rapid neuronal uptake, cytokine responses including enhanced production of tumor necrosis factor—α mRNA and protein and interleukin-6, neuronal oxidant stress (e.g. increased expression of hemoxygenase-1), and sustained reductions in cerebral blood flow (CBF). AP-induced cellular stress and cerebral vasospasm were blocked by circulating α-RAGE (40 μg/ml). In a chronic model, in 9-month old transgenic Tg APP sw+/−mice, CBF was significantly reduced by 63% in comparison to age-matched controls, this reduction was reversible by circulating α-RAGE in a dose-dependent fashion (10–40 μg/ml). In brains of subjects suffering from Alzheimer's disease, increased vascular expression of RAGE was associated with peri-vascular accumulation of Aβ, vascular and peri-vascular accumulation of proteins with nitrosylated amino-acid residues and increased expression of endothelial nitric oxide (NO) synthase. We conclude that vascular dysfunction caused by Aβ via RAGE at the BBB may contribute to ischemic changes and neurovascular injury in Alzheimer's dementia.

REFERENCES

1. Selkoe D J. The cell biology of beta-amyloid precursor protein and presenilin in Alzheimer's disease. Trends Cell Biol 1998; 8:447–53.
2. Younkin S G. The role of A beta 42 in Alzheimer's disease. J Physiol (Paris) 1998; 92:289–92.
3. Roses A D. Alzheimer disease: a model of gene mutations and susceptibility polymorphisms for complex psychiatric diseases. Amer J Med Gen 1998; 81:49–57.
4. Hardy J, Duff K, Hardy K G, Perez-Tur J, Hutton M. Genetic dissection of Alzheimer's disease and related dementias: amyloid and its relationship to tau. Nat Neurosci 1998; 1:355–8.
0.5. Pike C J, Burdick D, Walencewicz A J, Glabe C J, Cotman C W. Neurodegeneration induced by 9-amyloid peptides in vitro: the role of peptide assembly state. J Neurosci 1993;13:1676–87.
6. Ueda K, Fukui, Kageyama H. Amyloid beta protein-induced neuronal cell death: neurotoxic properties of aggregated amyloid beta protein. Brain Res 1994;639:240–4.
7. Lorenzo A, Yakner B A. Beta-amyloid neurotoxicity requires fibril formation and is inhibited by congo red. Proc Natl Acad Sci USA 1994;91:12243–7.
8. Kowall N W, Beal M F, Busciglio J, Duffy L K, Yankner B A. An in vivo model for the neurodegenerative effects of β amyloid and protection by substance P. Proc Natl Acad Sci USA 1991;88:7247–51.
9. Frautschy S A, Baird A, Cole G M. Effects of injected Alzheimers beta-amyloid cores in rat brain. Proc Natl Acad Sci USA 1991;88:8362–6
10. Kowall N W, McKee A C, Yankner B A, Beal M F. In vivo neurotoxicity of beta-amyloid [β(1–40)] and the β(25–35) fragment. Neurobiol Aging 1992;13:537–42.
11. Smith M A, Sayre L M, Monnier V M, Perry G. Radical AGEing in Alzheimer's disease. Trends Neurosci 1995;18:172–6.
12. Yan S D, Chen X, Fu J, Chen M, Zhu H, Roher A, Slattery T, Zhao L, Nagashima M, Morser J, Migheli A, Nawroth P, Stern D, Schmidt A M. RAGE and amyloid-9 peptide neurotoxicity in Alzheimer's disease. Nature 1996;382:685–91.
13. McGeer P L, McGeer E G. The inflammatory response system of brain: implications for therapy of Alzheimer and other neurodegenerative diseases. Brain Res Rev 1995;21:195–218.
14. Thomas T, Thomas G, McLendo C, Sutton T. Mullan M. β-Amyloid-mediated vasoactivity and vascular endothelial damage. Nature 1996;380:115–8.
15. Blanc E M, Toboreck M, Mark R J, Hennig B, Mattson M P. Amyloid 9-peptide induces cell monolayer albumin permeability, impairs glucose transport, and induces apoptosis in vascular endothelial cells. J Neurochem 1997;68 (5):1870–81.
16. Zlokovic B V. Can blood-brain barrier play a role in the development of cerebral amyloidosis and Alzheimer's disease pathology. Neurobiol Dis 1997;4(1):23–6.
17. Zlokovic B V, et al. Clearance of amyloid-b-peptide from brain: transport or metabolism? Nature Med. 6(7), 718–719
18. Maness L M, Banks W A, Podlisny M B, Selkoe D J, Kastin A J. Passage of human amyloid-β protein 1–40 across the murine blood-brain barrier. Life Sci 1994;55:1643–50.
19. Poduslo J F, Curran G L, Haggard J J, Biere A L, Selkoe D J. Permeability and residual plasma volume of human, Dutch variant, and rat amyloid B-protein 1–40 at the blood-brain barrier. Neurobiol Dis 1997;4(1):27–34.
20. Ghilardi J R, Catton M, Stimson E R, Rogers S, Walker L C, Maggio J E, Mantyh P W. Intra-arterial infusion of [$^{125}$I]Aβ1–40 labels amyloid deposits in the aged primate brain in vivo. Neuroreport 1996;7:2607–11.
21. Mackie J B, Weiss M H, Miao W, Ghiso J, Calero M, Bading J, Frangione B, Zlokovic B V. Cerebrovascular accumulation and increased blood-brain barrier permeability to circulationg Alzheimer's amyloid-s peptide in aged squirrel monkey with cerebral amyloid angiopathy. J Neurochem 1998;70:210–5.

22. Zlokovic B V, Martel C L, Matsubara E, McComb J G, Zheng G, McCluskey R T, Frangione B, Ghiso J. Glycoprotein 330/megalin: Probable role in receptor-mediated transport of apolipoprotein J alone and in a complex with Alzheimer's disease amyloid β at the blood-brain and blood-cerebrospinal fluid barriers. Proc Natl Acad Sci USA 1996;93:4229–36.

23. Martel C L, Mackic J B, Matsubara E, Governale S, Miguel C, Miao W, McComb J G, Frangione B, Ghiso J, Zlokovic B V. Isoform-specific effects of apolipoproteins E2, E3, E4 on cerebral capillary sequestration and blood-brain barrier transport of circulating Alzheimer's amyloid β. J Neurochem 1997;69:1995–2004.

24. Mackic J B, Stins M, McComb J G, Calero M, Ghiso J, Kim K S, Yan S D, Stern D, Schmidt A M, Frangione B, Zlokovic B V. Human blood-brain barrier receptors for Alzheimer's amyloid-β $_{1-40}$: asymmetrical binding, endocytosis and transcytosis at the apical side of brain microvascular endothelial cell monolayer. J Clin Invest 1998;102:734–743.

25. Ghersi-Egea J F, Gorevic P D, Ghiso J, Frangione B F, Patlak C S, Fenstermacher J D. Fate of cerebrospinal fluid-borne amyloid 1-peptide: rapid clearance into blood and appreciable accumulation by cerebral arteries J Neurochem 1996;67:880–83.

26. Yan S D, Zhu H, Zhu A, Golabek A, Du H, Roher A, Yu J, Soto C, Schmidt A M, Stern D, Kindy M. Receptor-dependent cell stress and amyloid accumulation in systemic amyloidosis. Nat Med 2000;6:643–51.

27. Hofmann M A, Drury S, Fu C, Qu W, Taguchi A, Lu Y, Avila C, Kambham N, Bierhaus A, Nawroth P, Neurath M F, Slattery T, Beach D, McClary J, Nagashima M, Morser J, Stern D, Schmidt A M. RAGE mediates a novel proinflammatory axis: a central cell surface receptor for S100/calgranulin polypeptides. Cell 1999;97:889–901.

28. Yan S D, Chen X, Fu J, Chen M, Zhu H, Roher A, Slattery T, Zhao L, Nagashima M, Morser J, Migheli A, Nawroth P, Stern D, Schmidt A M. RAGE and amyloid-β peptide neurotoxicity in Alzheimer's disease. Nature 1996;382:685–91.

29. Krieger M, Herz J. Structures and functions of multiligand lipoprotein receptors: macrophage scavenger receptors and LDL receptor-related protein (LRP). Annu Rev Biochem 1994;63:601–637.

30. Lucarelli M, Gennarelli M, Cardeli R, Cardeli R, Novelli G, Scarpa S, Dallapiccola B, Strom R. Expression of receptors for native and chemically modified low-density lipoproteins in brain microvessels. FEBS Lett 1997;401:53–8.

31. Schmidt A M, Hasu M, Popov D, Zhang J H, Chen J, Yan S D, Brett J, Cao R, Kuwabara K, Gostache G, Simionescu N, 9 Simionescu M, Stern D. Receptor for advanced glycation end products (AGE) has a central role in vessel wall interactions and gene activation in response to circulating AGE proteins. Proc Natl Acad Sci USA 1994;91:8807–11.

35. Holtzman D M, Bales K R, Wu S, Bhat P, Parsadanian M, Fagan Am, Chang L K, Sun Y, Paul S M. In Vivo expression of apolipoprotein E reduces amyloid-β-deposition in a mouse model of Alzheimer's Disease. J Clin Invest 1999; 103:R15–21.

36. Tabrizi et Zlokovic, BV., ATVB, 1999

37. Maeda K, Mies G, Olah L, Hossmann K A. Quantitative measurement of local cerebral blood flow in the anesthetized mouse using intraperitoneal [14C]iodoantipyrine injection and final arterial heart blood sampling. J Cereb Blood Flow Metab 2000;20:10–4.

38. Zlokovic B V. Cerebrovascular permeability to peptides: manipulations of transport systems at the blood-brain barrier. Pharm Res 1995; 12(10): 1395–1406.

39. Zlokovic B V, Jovanovic S, Miao W, Samara S, Verma S, Farrell C L. Differential regulation of leptin transport by the choroid plexus and blood-brain barrier and high affinity transport systems for entry into hypothalamus and across the blood-cerebrospinal fluid barrier. Endocrinology 2000;141:1434–41.

40. Zlokovic B V, Begley D J, Djuricic B M, Mitrovic D M. Measurement of solute transport across the blood-brain barrier in the perfused guinea pig brain: method and application to N-methyl-alpha-aminoisobutyric acid. J Neurochem 1986;46:1444–51.

---

What is claimed is:

1. A method for decreasing cerebral vasoconstriction in a subject suffering from an Alzheimer's disease-type pathology, which comprises administering to the subject an inhibitor of receptor for advanced glycation endproduct (RAGE) in an effective amount to inhibit transcytosis of amyloid-β peptides across the blood-brain barrier in the subject, thereby decreasing cerebral vasoconstriction in the subject.

2. The method of claim 1, wherein the subject is a human subject.

3. The method of claim 1, wherein the subject suffers from Alzheimer's disease.

4. The method of claim 1, wherein the inhibitor is a molecule having a molecular weight from about 500 daltons to about 100 kilodaltons.

5. The method of claim 1, wherein the inhibitor is an organic molecule or an inorganic molecule.

6. The method of claim 1, wherein the inhibitor is a polypeptide or a nucleic acid molecule.

7. The method of claim 1, wherein the inhibitor is soluble receptor for advanced glycation endproduct.

8. The method of claim 1, wherein the inhibitor is an antibody which specifically binds to receptor for advanced glycation endproduct.

9. A method for treating Alzheimer's disease in a subject which comprises administering to the subject an effective amount of an inhibitor of receptor for advanced glycation endproduct (RAGE) activity so as to increase cerebral blood flow in the subject and thereby treat Alzheimer's disease in the subject.

* * * * *

SEQUENCE LISTING

```
<160> NUMBER OF SEQ ID NOS:  6

<210> SEQ ID NO 1
<211> LENGTH: 416
<212> TYPE: PRT
<213> ORGANISM: Bos Taurus

<400> SEQUENCE: 1

Met Ala Ala Gly Ala Val Val Gly Ala Trp Met Leu Val Leu Ser Leu
  1               5                  10                  15

Gly Gly Thr Val Thr Gly Asp Gln Asn Ile Thr Ala Arg Ile Gly Lys
             20                  25                  30

Pro Leu Val Leu Asn Cys Lys Gly Ala Pro Lys Lys Pro Pro Gln Gln
         35                  40                  45

Leu Glu Trp Lys Leu Asn Thr Gly Arg Thr Glu Ala Trp Lys Val Leu
     50                  55                  60

Ser Pro Gln Gly Asp Pro Trp Asp Ser Val Ala Arg Val Leu Pro Asn
 65                  70                  75                  80

Gly Ser Leu Leu Leu Pro Ala Val Gly Ile Gln Asp Glu Gly Thr Phe
```

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |
| Arg | Cys | Arg | Ala | Thr | Ser | Arg | Ser | Gly | Lys | Glu | Thr | Lys | Ser | Asn | Tyr |

Arg Cys Arg Ala Thr Ser Arg Ser Gly Lys Glu Thr Lys Ser Asn Tyr
                100                     105                 110

Arg Val Arg Val Tyr Gln Ile Pro Gly Lys Pro Glu Ile Val Asp Pro
            115                 120                 125

Ala Ser Glu Leu Met Ala Gly Val Pro Asn Lys Val Gly Thr Cys Val
        130                 135             140

Ser Glu Gly Gly Tyr Pro Ala Gly Thr Leu Asn Trp Leu Leu Asp Gly
145                 150                 155                 160

Lys Thr Leu Ile Pro Asp Gly Lys Gly Val Ser Val Lys Glu Glu Thr
                165                 170                 175

Lys Arg His Pro Lys Thr Gly Leu Phe Thr Leu His Ser Glu Leu Met
            180                 185                 190

Val Thr Pro Ala Arg Gly Gly Ala Leu His Pro Thr Phe Ser Cys Ser
        195                 200                 205

Phe Thr Pro Gly Leu Pro Arg Arg Ala Leu His Thr Ala Pro Ile
    210                 215                 220

Gln Leu Arg Val Trp Ser Glu His Arg Gly Glu Gly Pro Asn Val
225                 230                 235                 240

Asp Ala Val Pro Leu Lys Glu Val Gln Leu Val Glu Pro Glu Gly
                245                 250                 255

Gly Ala Val Ala Pro Gly Gly Thr Val Thr Leu Thr Cys Glu Ala Pro
            260                 265                 270

Ala Gln Pro Pro Gln Ile His Trp Ile Lys Asp Gly Arg Pro Leu
        275                 280                 285

Pro Leu Pro Pro Gly Pro Met Leu Leu Leu Pro Glu Val Gly Pro Glu
    290                 295                 300

Asp Gln Gly Thr Tyr Ser Cys Val Ala Thr His Pro Ser His Gly Pro
305                 310                 315                 320

Gln Glu Ser Arg Ala Val Ser Val Thr Ile Glu Thr Gly Glu Glu
                325                 330                 335

Gly Thr Thr Ala Gly Ser Val Glu Gly Pro Gly Leu Glu Thr Leu Ala
            340                 345                 350

Leu Thr Leu Gly Ile Leu Gly Gly Leu Gly Thr Val Ala Leu Leu Ile
        355                 360                 365

Gly Val Ile Val Trp His Arg Arg Gln Arg Lys Gly Gln Glu Arg
    370                 375                 380

Lys Val Pro Glu Asn Gln Glu Glu Glu Glu Glu Arg Ala Glu Leu
385                 390                 395                 400

Asn Gln Pro Glu Glu Pro Glu Ala Ala Glu Ser Ser Thr Gly Gly Pro
                405                 410                 415

<210> SEQ ID NO 2
<211> LENGTH: 1426
<212> TYPE: DNA
<213> ORGANISM: Bos Taurus

<400> SEQUENCE: 2
cggagaagga tggcagcagg ggcagtggtc ggagcctgga tgctagtcct cagtctgggg      60
gggacagtca cggggaccaa aacatcaca gcccggatcg ggaagccact ggtgctgaac      120
tgcaagggag cccccaagaa accaccccag cagctggaat ggaaactgaa cacaggccgg      180
acagaagctt ggaaagtcct gtctccccag ggagaccct gggatagcgt ggctcgggtc      240
ctccccaacg gctccctcct cctgccggct gttgggatcc aggatgaggg gactttccgg      300

-continued

```
tgccgggcaa cgagccggag cggaaaggag accaagtcta actaccgagt ccgagtctat    360
cagattcctg ggaagccaga aattgttgat cctgcctctg aactcatggc tggtgtcccc    420
aataaggtgg ggacatgtgt gtccgagggg ggctaccctg cagggactct taactggctc    480
ttggatggga aaactctgat tcctgatggc aaggagtgt cagtgaagga agagaccaag    540
agacacccaa agacagggct tttcacgctc cattcggagc tgatggtgac ccagctcgg    600
ggaggagctc tccaccccac cttctcctgt agcttcaccc ctggccttcc ccggcgccga    660
gccctgcaca cggcccccat ccagctcagg gtctggagtg agcaccgagg tggggagggc    720
cccaacgtgg acgctgtgcc actgaaggaa gtccagttgg tggtagagcc agaaggggga    780
gcagtagctc ctggtggtac tgtgaccttg acctgtgaag cccccgccca gcccccacct    840
caaatccact ggatcaagga tggcaggccc ctgccccttc ccctggccc catgctgctc    900
ctcccagagg tagggcctga ggaccaggga acctacagtt gtgtggccac ccatcccagc    960
catgggcccc aggagagccg tgctgtcagc gtcacgatca tcgaaacagg cgaggagggg   1020
acgactgcag gctctgtgga agggccgggg ctggaaaccc tagccctgac cctggggatc   1080
ctgggaggcc tggggacagt cgccctgctc attggggtca tcgtgtggca tcgaaggcgg   1140
caacgcaaag gacaggagag gaaggtcccg gaaaaccagg aggaggaaga ggaggagaga   1200
gcggaactga accagccaga ggagcccgag gcggcagaga gcagcacagg agggccttga   1260
ggagcccacg gccagacccg atccatcagc ccctttctt ttcccacact ctgttctggc   1320
cccagaccag ttctcctctg tataatctcc agcccacatc tcccaaactt tcttccacaa   1380
ccagagcctc ccacaaaaag tgatgagtaa acacctgcca cattta                  1426
```

<210> SEQ ID NO 3
<211> LENGTH: 404
<212> TYPE: PRT
<213> ORGANISM: Human

<400> SEQUENCE: 3

```
Gly Ala Ala Gly Thr Ala Val Gly Ala Trp Val Leu Val Leu Ser Leu
 1               5                  10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Arg Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175
```

Thr Arg Arg His Pro Glu Thr Gly Leu Phe Thr Leu Gln Ser Glu Leu
        180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
        210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
        290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
                325                 330                 335

Gly Leu Gly Thr Leu Ala Leu Ala Leu Gly Ile Leu Gly Gly Leu Gly
            340                 345                 350

Thr Ala Ala Leu Leu Ile Gly Val Ile Leu Trp Gln Arg Arg Gln Arg
        355                 360                 365

Arg Gly Glu Glu Arg Lys Ala Pro Glu Asn Gln Glu Glu Glu Glu Glu
        370                 375                 380

Arg Ala Glu Leu Asn Gln Ser Glu Glu Pro Glu Ala Gly Glu Ser Ser
385                 390                 395                 400

Thr Gly Gly Pro

<210> SEQ ID NO 4
<211> LENGTH: 1391
<212> TYPE: DNA
<213> ORGANISM: Human

<400> SEQUENCE: 4 gggcagccg gaacagcagt tggagcctgg gtgctggtcc tcagtctgtg gggggcagta      60
gtaggtgctc aaaacatcac agcccggatt ggcgagccac tggtgctgaa gtgtaagggg    120
gcccccaaga aaccacccca gcggctggaa tggaaactga acacaggccg acagaagct    180 tggaaggtcc tgtctcccca gggaggaggc ccctgggaca gtgtggctcg tgtccttccc    240
aacggctccc tcttccttcc ggctgtcggg atccaggatg aggggatttt ccggtgcagg    300
gcaatgaaca ggaatggaaa ggagaccaag tccaactacc gagtccgtgt ctaccagatt    360
cctgggaagc cagaaattgt agattctgcc tctgaactca cggctggtgt tcccaataag    420
gtggggacat gtgtgtcaga gggaagctac cctgcaggga ctcttagctg cacttggat     480 gggaagcccc tggtgcctaa tgagaaggga gtatctgtga aggaacagac caggagacac    540
cctgagacag gctcttcac actgcagtcg gagctaatgg tgaccccagc ccggggagga    600 gatcccgtc ccaccttctc ctgtagcttc agcccaggcc ttccccgaca ccgggccttg    660
cgcacagccc ccatccagcc ccgtgtctgg agcctgtgc ctctggagga ggtccaattg    720
gtggtggagc cagaaggtgg agcagtagct cctggtggaa ccgtaaccct gacctgtgaa    780

-continued

```
gtccctgccc agccctctcc tcaaatccac tggatgaagg atggtgtgcc cttgcccctt    840 cccccagcc ctgtgctgat cctccctgag atagggcctc aggaccaggg aacctacagc    900
tgtgtggcca cccattccag ccacgggccc caggaaagcc gtgctgtcag catcagcatc    960
atcgaaccag gcgaggaggg gccaactgca ggctctgtgg gaggatcagg gctgggaact   1020
ctagccctgg ccctggggat cctgggaggc ctggggacag ccgccctgct cattggggtc   1080
atcttgtggc aaaggcggca acgccgagga gaggagagga aggccccaga aaaccaggag   1140
gaagaggagg agcgtgcaga actgaatcag tcggaggaac ctgaggcagg cgagagtagt   1200
actggagggc cttgaggggc ccacagacag atcccatcca tcagctccct tttcttttc    1260 ccttgaactg ttctggcctc agaccaactc tctcctgtat aatctctctc ctgtataacc   1320
ccaccttgcc aagctttctt ctacaaccag agccccccac aatgatgatt aaacacctga   1380
cacatcttgc a                                                         1391
```

<210> SEQ ID NO 5
<211> LENGTH: 403
<212> TYPE: PRT
<213> ORGANISM: Mouse

<400> SEQUENCE: 5

```
Met Pro Ala Gly Thr Ala Ala Arg Ala Trp Val Leu Val Leu Ala Leu
  1               5                  10                  15

Trp Gly Ala Val Ala Gly Gly Gln Asn Ile Thr Ala Arg Ile Gly Glu
                 20                  25                  30

Pro Leu Val Leu Ser Cys Lys Gly Ala Pro Lys Lys Pro Pro Gln Gln
             35                  40                  45

Leu Glu Trp Lys Leu Asn Thr Gly Arg Thr Glu Ala Trp Lys Val Leu
         50                  55                  60

Ser Pro Gln Gly Gly Pro Trp Asp Ser Val Ala Gln Ile Leu Pro Asn
 65                  70                  75                  80

Gly Ser Leu Leu Leu Pro Ala Thr Gly Ile Val Asp Glu Gly Thr Phe
                 85                  90                  95

Arg Cys Arg Ala Thr Asn Arg Arg Gly Lys Glu Val Lys Ser Asn Tyr
            100                 105                 110

Arg Val Arg Val Tyr Gln Ile Pro Gly Lys Pro Glu Ile Val Asp Pro
        115                 120                 125

Ala Ser Glu Leu Thr Ala Ser Val Pro Asn Lys Val Gly Thr Cys Val
    130                 135                 140

Ser Glu Gly Ser Tyr Pro Ala Gly Thr Leu Ser Trp His Leu Asp Gly
145                 150                 155                 160

Lys Leu Leu Ile Pro Asp Gly Lys Glu Thr Leu Val Lys Glu Glu Thr
                165                 170                 175

Arg Arg His Pro Glu Thr Gly Leu Phe Thr Leu Arg Ser Glu Leu Thr
            180                 185                 190

Val Ile Pro Thr Gln Gly Gly Thr Thr His Pro Thr Phe Ser Cys Ser
        195                 200                 205

Phe Ser Leu Gly Leu Pro Arg Arg Arg Pro Leu Asn Thr Ala Pro Ile
    210                 215                 220

Gln Leu Arg Val Arg Glu Pro Gly Pro Glu Gly Ile Gln Leu Leu
225                 230                 235                 240

Val Glu Pro Glu Gly Gly Ile Val Ala Pro Gly Gly Thr Val Thr Leu
                245                 250                 255

Thr Cys Ala Ile Ser Ala Gln Pro Pro Pro Gln Val His Trp Ile Lys
```

-continued

|  |  |  |  | 260 |  |  |  | 265 |  |  |  | 270 |  |
|---|---|---|---|---|---|---|---|---|---|---|---|---|---|
| Asp | Gly | Ala | Pro | Leu | Pro | Leu | Ala | Pro | Ser | Pro | Val | Leu | Leu | Pro |
|  |  | 275 |  |  |  | 280 |  |  |  | 285 |  |  |  |

Glu Val Gly His Ala Asp Glu Gly Thr Tyr Ser Cys Val Ala Thr His
        290                 295                 300

Pro Ser His Gly Pro Gln Glu Ser Pro Pro Val Ser Ile Arg Val Thr
305                 310                 315                 320

Glu Thr Gly Asp Glu Gly Pro Ala Glu Gly Ser Val Gly Glu Ser Gly
                325                 330                 335

Leu Gly Thr Leu Ala Leu Ala Leu Gly Ile Leu Gly Gly Leu Gly Val
            340                 345                 350

Val Ala Leu Leu Val Gly Ala Ile Leu Trp Arg Lys Arg Gln Pro Arg
        355                 360                 365

Arg Glu Glu Arg Lys Ala Pro Glu Ser Gln Glu Asp Glu Glu Glu Arg
    370                 375                 380

Ala Glu Leu Asn Gln Ser Glu Glu Ala Glu Met Pro Glu Asn Gly Ala
385                 390                 395                 400

Gly Gly Pro

<210> SEQ ID NO 6
<211> LENGTH: 1347
<212> TYPE: DNA
<213> ORGANISM: Mouse

<400> SEQUENCE: 6

```
gcaccatgcc agcggggaca gcagctagag cctgggtgct ggttcttgct ctatggggag    60
ctgtagctgg tggtcagaac atcacagccc ggattggaga gccacttgtg ctaagctgta   120
agggggcccc taagaagccg ccccagcagc tagaatggaa actgaacaca ggaagaactg   180
aagcttggaa ggtcctctct ccccaggagg ccccctggga cagcgtgcgt caaatcctcc   240
ccaatggttc cctcctcctt ccagccactg gaattgtcga tgaggggacg ttccggtgtc   300
gggcaactaa caggcgaggg aaggaggtca agtccaacta ccgagtccga gtctaccaga   360
ttcctgggaa gccagaaatt gtggatcctg cctctgaact cacagccagt gtccctaata   420
aggtggggac atgtgtgtct gagggaagct accctgcagg gacccttagc tggcacttag   480
atgggaaact tctgattccc gatggcaaag aaacactcgt gaaggaagag accaggagac   540
accctgagac gggactcttt acactgcggt cagagctgac agtgatcccc acccaaggag   600
gaaccaccca tcctaccttc tcctgcagtt tcagcctggg ccttccccgg cgcagacccc   660
tgaacacagc cctatccaa ctccgagtca gggagcctgg gcctccagag ggcattcagc   720
tgttggttga gcctgaaggt ggaatagtcg ctcctggtgg gactgtgacc ttgacctgtg   780
ccatctctgc ccagccccct cctcaggtcc actggataaa ggatggtgca cccttgcccc   840
tggctcccag ccctgtgctg ctcctccctg aggtggggca cgcggatgag ggcacctata   900
gctgcgtggc cacccaccct agccacggac ctcaggaaag ccctcctgtc agcatcaggg   960
tcacagaaac cggcgatgag gggccagctg aaggctctgt gggtgagtct ggctgggta   1020
cgctagccct ggccttgggg atcctgggag cctgggagt agtagccctg ctcgtcgggg   1080
ctatcctgtg gcgaaaacga caacccaggc gtgaggagag gaaggcccct gaaagccagg   1140
aggatgagga ggaacgtgca gagctgaatc agtcagagga gcggagatg ccagagaatg   1200
gtgccggggg accgtaagag cacccagatc gagcctgtgt gatggcccta gagcagctcc   1260
```

```
                                                    -continued cccacattcc atcccaattc ctccttgagg cacttccttc tccaaccaga gcccacatga    1320
ccatgctgag taaacatttg atacggc                                        1347
```